US00PP27343P2

(12) United States Plant Patent
Sakazaki

(10) Patent No.: US PP27,343 P2
(45) Date of Patent: Nov. 1, 2016

(54) ***PETUNIA* PLANT NAMED 'USTUN60501'**

(50) Latin Name: *Petunia×hybrida*
Varietal Denomination: USTUN60501

(71) Applicant: Ushio Sakazaki, Shiga (JP)

(72) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 174 days.

(21) Appl. No.: 14/121,648

(22) Filed: Oct. 1, 2014

(51) Int. Cl.
*A01H 5/02* (2006.01)

(52) U.S. Cl.
USPC ..... Plt./356.2

(58) Field of Classification Search
USPC ..... Plt./356.19, 356.2
See application file for complete search history.

*Primary Examiner* — Keith Robinson
(74) *Attorney, Agent, or Firm* — C. A. Whealy

(57) ABSTRACT

A new and distinct *Petunia* plant named 'USTUN60501', characterized by its compact, outwardly spreading to trailing plant habit; freely branching habit; vigorous growth habit; early and freely flowering habit; dark violet-colored flowers; and good garden performance.

1 Drawing Sheet

Botanical designation: *Petunia×hybrida.*
Cultivar denomination: 'USTUN60501'.

BACKGROUND OF THE INVENTION

The present invention relates to a new and distinct cultivar of *Petunia* plant, botanically known as *Petunia×hybrida* and hereinafter referred to by the name 'USTUN60501'.

The new *Petunia* plant is a product of a planned breeding program conducted by the Inventor in Higashiomi, Shiga, Japan and Bonsall, Calif. The objective of the breeding program is to create new freely-branching and uniformly mounding *Petunia* plants with early and freely flowering habit, unique attractive flowers and good garden performance.

The new *Petunia* plant originated from a cross-pollination made by the Inventor on May 6, 2011 in Higashiomi, Shiga, Japan of *Petunia×hybrida* 'Surfinia Cutie Blue', not patented, as the female, or seed, parent with a proprietary seedling selection of *Petunia×hybrida* identified as code number 11PJ03, not patented, as the male, or pollen, parent. The new *Petunia* plant was discovered and selected by the Inventor as a single flowering plant within the progeny of the stated cross-pollination in a controlled greenhouse environment in Bonsall, Calif. on May 24, 2012.

Asexual reproduction of the new *Petunia* plant by vegetative cuttings in a controlled greenhouse environment in Bonsall, Calif. since May 26, 2012 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'USTUN60501'. These characteristics in combination distinguish 'USTUN60501' as a new and distinct *Petunia* plant:

1. Compact, outwardly spreading to trailing plant habit.
2. Freely branching habit.
3. Vigorous growth habit.
4. Early and freely flowering habit.
5. Dark violet-colored flowers.
6. Good garden performance.

Plants of the new *Petunia* can be compared to plants of the female parent, 'Surfinia Cutie Blue'. In side-by-side comparisons conducted in Bonsall, Calif., plants of the new *Petunia* differ primarily from plants of 'Surfinia Cutie Blue' in the following characteristics:

1. Plants of the new *Petunia* are more spreading than and not as upright as plants of 'Surfinia Cutie Blue'.
2. Plants of the new *Petunia* are more vigorous than plants of 'Surfinia Cutie Blue'.
3. Plants of the new *Petunia* and 'Surfinia Cutie Blue' differ in flower color as plants of 'Surfinia Cutie Blue' have light blue-colored flowers.

Plants of the new *Petunia* can be compared to plants of the male parent selection. In side-by-side comparisons conducted in Bonsall, Calif., plants of the new *Petunia* differ primarily from plants of the male parent selection in the following characteristics:

1. Plants of the new *Petunia* are more spreading and mounding than and not as creeping as plants of the male parent selection.
2. Plants of the new *Petunia* and the male parent selection differ in flower color as plants of the male parent selection have bluish purple-colored flowers.

Plants of the new *Petunia* can be compared to plants of 'USTUN29801', disclosed in U.S. Plant Pat. No. 22,883. In side-by-side comparisons conducted in Bonsall, Calif., plants of the new *Petunia* differed primarily from plants of 'USTUN29801' in the following characteristics:

1. Plants of the new *Petunia* flowered earlier than plants of 'USTUN29801'.
2. Plants of the new *Petunia* were more freely flowering than plants of 'USTUN29801'.

Plants of the new *Petunia* can also be compared to plants of 'KEllavbu', disclosed in U.S. Plant Pat. No. 13,542. In side-by-side comparisons, plants of the new *Petunia* differed primarily from plants of 'KEllavbu' in the following characteristics:

1. Plants of the new *Petunia* were more spreading and mounded than and not as creeping as plants of 'KEllavbu'.
2. Plants of the new *Petunia* had smaller flowers than plants of 'KEllavbu'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the bottom of the sheet comprises a side perspective view of a typical plant of 'USTUN60501' grown in a container.

The photograph at the top of the sheet is a close-up view of a typical flowering plant of 'USTUN60501'.

DETAILED BOTANICAL DESCRIPTION

The aforementioned photographs and following observations, measurements and values describe plants grown during the spring in 11.5-cm containers in a polyethylene-covered greenhouse and subsequently in an outdoor nursery in Bonsall, Calif. During the production of the plants, day temperatures averaged 24° C. and night temperatures ranged from 13° C. to 16° C. Plants were pinched two times and were six weeks old when the photographs and description were taken. In the following description, color references are made to The Royal Horticultural Society Colour Chart, 2007 Edition, except where general terms of ordinary dictionary significance are used.

Botanical classification: *Petunia×hybrida* 'USTUN60501'.

Parentage:

*Female, or seed, parent.*—*Petunia×hybrida* 'Surfinia Cutie Blue', not patented.

*Male, or pollen, parent.*—Proprietary seedling selection of *Petunia×hybrida* identified as code number 11PJ03, not patented.

Propagation:

*Type.*—Terminal vegetative cuttings.

*Time to produce a rooted young plant, summer.*—About 15 days at temperatures ranging from 16° C. to 29° C.

*Time to produce a rooted young plant, winter.*—About 20 days at temperatures ranging from 16° C. to 21° C.

*Root description.*—Medium in thickness, fibrous.

*Rooting habit.*—Freely branching; medium density.

Plant description:

*Plant and growth habit.*—Compact, outwardly spreading to trailing plant habit; freely branching habit with about ten primary lateral branches with multiple secondary lateral branches developing per plant; dense and bushy appearance; pinching enhances development of lateral branches; vigorous growth habit.

*Plant height.*—About 15 cm.

*Plant diameter (area of spread).*—About 34 cm.

*Lateral branches.*—Length: About 19 cm. Diameter: About 2 mm. Internode length: About 1.5 cm. Strength: Strong. Aspect: Initially upright then outwardly spreading. Texture: Pubescent. Color: Close to 146A.

Leaf description:

*Arrangement.*—Alternate before flowering; opposite after flowers develop; leaves simple.

*Length.*—About 3.6 cm.

*Width.*—About 1.8 cm.

*Shape.*—Elliptical.

*Apex.*—Broadly acute.

*Base.*—Attenuate.

*Margin.*—Entire.

*Texture, upper and lower surfaces.*—Pubescent; glandular.

*Venation pattern.*—Pinnate, arcuate.

*Color.*—Developing leaves, upper surface: Close to 137B. Developing leaves, lower surface: Close to 146B. Fully expanded leaves, upper surface: Close to 137A; venation, close to 146C. Fully expanded leaves, lower surface: Close to 146B; venation, close to 146C.

*Petioles.*—Length: About 9 mm. Diameter: About 1.5 mm. Texture, upper and lower surfaces: Pubescent; minute. Color, upper surface: Close to 146B. Color, lower surface: Close to 147C.

Flower description:

*Flower type and flowering habit.*—Single axillary salverform flowers; flowers face mostly upward to outwardly; freely flowering habit with about twelve open flowers per lateral branch and more than 250 flowers developing per plant.

*Natural flowering season.*—Long day responsive; long flowering period, plants flower from early spring until frost in the autumn, flowering continuous during this period; early flowering habit, plants begin flowering about four to six weeks after planting.

*Flower longevity on the plant.*—About four to five days; flowers persistent.

*Fragrance.*—None detected.

*Flower buds.*—Length: About 3.3 cm. Diameter: About 6 mm. Shape: Oblong. Color: Close to N77C.

*Flower diameter.*—About 3.4 cm.

*Flower depth (height).*—About 4.2 cm.

*Throat diameter, distal.*—About 8 mm.

*Tube length.*—About 3 cm.

*Tube diameter, proximal.*—About 3 mm.

*Petals.*—Quantity and arrangement: Five petals fused in a single salverform whorl. Petal lobe length (from throat): About 1.5 cm. Petal lobe width: About 1.6 cm. Petal lobe shape: Fan-shaped. Petal lobe apex: Broadly acute. Petal lobe margin: Entire. Petal lobe texture, upper surface: Smooth, glabrous; velvety. Petal lobe texture, lower surface: Mostly smooth with scattered minute pubescence. Throat texture: Smooth, glabrous. Tube texture: Pubescent. Color: When opening, upper surface: Close to 83A. When opening, lower surface: Close to 79D. Fully opened, upper surface: Close to 83B; venation, close to 83A; color does not change with development. Fully opened, lower surface: Close to 86C; venation, close to 83B. Flower throat (inside): Close to 83A; venation, close to 79A. Flower tube (outside): Close to N92A; venation, close to 79A.

*Sepals*.—Quantity and arrangement: Five sepals fused in a single star-shaped whorl. Length: About 1.4 cm. Width: About 2 mm. Shape: Lanceolate. Apex: Rounded. Margin: Entire. Texture, upper and lower surfaces: Pubescent; minute. Color, upper surface: Close to 146A. Color, lower surface: Close to 146B.

*Peduncles*.—Length: About 2.2 cm. Width: About 1 mm. Angle: About 45° from the stem axis. Strength: Strong. Texture: Pubescent; minute. Color: Close to 146C.

*Reproductive organs*.—Stamens: Quantity per flower: Five. Filament length: About 1.8 cm. Filament color: Close to 84C. Anther length: About 2 mm. Anther shape: Oval. Anther color: Close to 91A. Pollen amount: Moderate. Pollen color: Close to 94B. Pistils: Quantity per flower: One. Pistil length: About 1.9 cm. Style length: About 1.6 cm. Style color: Close to 145D. Stigma shape: Round. Stigma color: Close to N77A. Ovary color: Close to 145A.

*Seeds and fruits*.—Seed and fruit development has not been observed on plants of the new *Petunia*.

Pathogen & pest resistance: Plants of the new *Petunia* have not been noted to be resistant to pathogens or pests common to *Petunia* plants.

Garden performance: Plants of the new *Petunia* have been observed to have good garden performance and have been observed to tolerate rain, wind and temperatures ranging from about 1° C. to about 40° C.

It is claimed:

1. A new and distinct *Petunia* plant named 'USTUN60501' as illustrated and described.

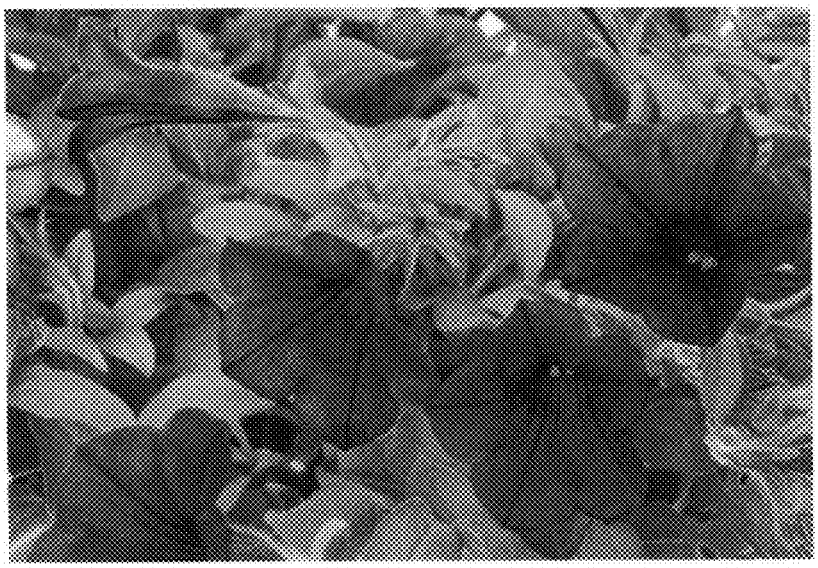
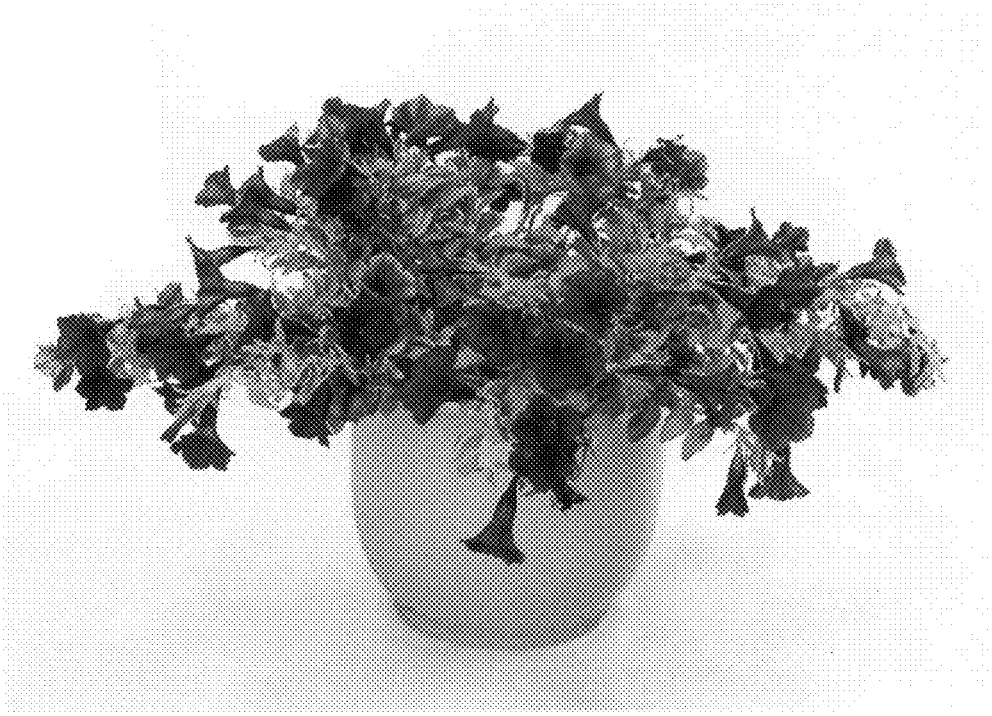

* * * * *